United States Patent
Kim et al.

(10) Patent No.: US 10,226,182 B2
(45) Date of Patent: Mar. 12, 2019

(54) PHOTOACOUSTIC PROBE AND PHOTOACOUSTIC DIAGNOSTIC APPARATUS INCLUDING SAME

(71) Applicants: SAMSUNG MEDISON CO., LTD., Hongcheon-gun, Gangwon-do (KR); SAMSUNG ELECTRONICS CO., LTD., Suwon-si, Gyeonggi-do (KR)

(72) Inventors: Jung-Ho Kim, Seoul (KR); Dal-kwon Koh, Suwon-si (KR); Jong-kyu Jung, Seoul (KR); Jung-taek Oh, Seoul (KR); Jae-kwang Lee, Hwaseong-si (KR)

(73) Assignees: SAMSUNG MEDISON CO., LTD., Hongcheon-gun, Gangwon-do (KR); SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 871 days.

(21) Appl. No.: 14/449,843

(22) Filed: Aug. 1, 2014

(65) Prior Publication Data
US 2015/0126849 A1    May 7, 2015

(30) Foreign Application Priority Data
Nov. 4, 2013    (KR) .................. 10-2013-0132993

(51) Int. Cl.
*A61B 5/00*     (2006.01)
*G01N 21/17*    (2006.01)
*A61B 8/00*     (2006.01)

(52) U.S. Cl.
CPC ....... *A61B 5/0095* (2013.01); *G01N 21/1702* (2013.01); *A61B 8/4444* (2013.01); *G01N 2021/1706* (2013.01); *G01N 2021/1708* (2013.01)

(58) Field of Classification Search
CPC .................................................. G01N 21/1702
See application file for complete search history.

(56) References Cited

U.S. PATENT DOCUMENTS 3,476,029 A * 11/1969 Schreckendgust ...... G02F 1/172
                                                                359/275
6,498,942 B1  12/2002 Esenaliev et al.
8,300,224 B2  10/2012 Nakajima et al.
(Continued)

FOREIGN PATENT DOCUMENTS

CN    102858232 A    1/2013
CN    103345770 A    10/2013
(Continued)

OTHER PUBLICATIONS

Machine translation of Kasamatsu et al. (JPO Pub. No. JP 2012-173246 A, Sep. 10, 2012).*
(Continued)

*Primary Examiner* — Carolyn Pehlke
(74) *Attorney, Agent, or Firm* — McDermott Will & Emery LLP (57) ABSTRACT

Provided is a photoacoustic probe. The photoacoustic probe is configured to control light emitted from an optical unit by using a shutter that is switched between a state in which the shutter is opened to allow light to pass therethrough and a state in which the shutter blocks the light according to whether an inspection starts.

4 Claims, 11 Drawing Sheets

(56) References Cited

U.S. PATENT DOCUMENTS

| | | | |
|---|---|---|---|
| 2008/0249380 A1* | 10/2008 | Van Beek | A61B 5/0059 600/310 |
| 2009/0163787 A1* | 6/2009 | Mannheimer | A61B 5/14552 600/324 |
| 2012/0302865 A1 | 11/2012 | Tokita et al. | |
| 2013/0281819 A1 | 10/2013 | Schmid | |
| 2014/0018661 A1 | 1/2014 | Tsujita et al. | |
| 2014/0051971 A1 | 2/2014 | Tokita | |
| 2014/0114169 A1 | 4/2014 | Sato | |
| 2014/0206978 A1* | 7/2014 | Ackerman | A61B 5/0095 600/407 |

FOREIGN PATENT DOCUMENTS

| | | |
|---|---|---|
| JP | 61-185404 U | 11/1986 |
| JP | 2007-536053 A | 12/2007 |
| JP | 2012/086037 A | 5/2012 |
| JP | 2012-173246 A | 9/2012 |
| JP | 2012-205886 A | 10/2012 |
| JP | 2012-231978 A | 11/2012 |
| KR | 10-2010-0055676 A | 5/2010 |
| KR | 10-2012-0118261 A | 10/2012 |
| WO | 98/22150 A1 | 5/1998 |
| WO | 2012/102036 A1 | 8/2012 |
| WO | 2012/117719 | 9/2012 |

OTHER PUBLICATIONS

Meadowlark Catalog (http://www.meadowlark.com/store/catalog/Catalog_Oct_18_2012.pdf, Oct. 18, 2012).*
Korean Notice of Non-Final Rejection issued in Korean Application No. 10-2013-0132993 dated Jan. 5, 2015, with English Translation.
Extended European Search Report issued in European Patent Application No. 14162748.9 dated Mar. 11, 2015.
Fronheiser, M.P., "Real-time optoacoustic monitoring and three-dimensional mapping of a human arm vasculature", Journal of Biomedical Optics, Mar./Apr. 2010, 15(2), pp. 021305-1-021305-7.
Korean Office Action issued in Application No. 10-2015-0031122 dated May 21, 2015, with English Translation.
Korean Notice of Allowance issued in Application No. 10-2013-0132993 dated Jul. 21, 2015, with English Translation.
Korean Office Action issued in Korean Application No. 10-2015-0031122 dated Nov. 26, 2015, with English Translation.
Chinese Office Action dated Jul. 18, 2018 issued in Chinese Patent Application No. 201410397480.X (with English translation).

* cited by examiner

PHOTOACOUSTIC PROBE AND PHOTOACOUSTIC DIAGNOSTIC APPARATUS INCLUDING SAME

RELATED APPLICATIONS

This application claims the benefit of Korean Patent Application No. 10-2013-0132993, filed on Nov. 4, 2013, in the Korean Intellectual Property Office, the disclosure of which is incorporated herein in its entirety by reference.

BACKGROUND

1. Field

One or more embodiments of the present invention relate to a photoacoustic probe and a photoacoustic diagnostic apparatus including the same that are used in diagnosis from photoacoustic images.

2. Description of the Related Art

A photoacoustic imaging technology uses a photoacoustic effect to noninvasively image biological tissues. When a biological tissue is irradiated with a short electromagnetic laser pulse for photoacoustic imaging, some of the optical energy from the laser pulse is absorbed by the biological tissue and subsequently converted into heat, thereby causing transient thermo-elastic expansion. The thermo-elastic expansion leads to emission of wideband ultrasound waves, and the emitted ultrasound waves are detected by ultrasound transducers from different directions and reconstructed into images.

Since photoacoustic imaging is based on the conversion of optical energy into ultrasound waves for detection, this method has advantages of combining properties of optical imaging with those of ultrasound imaging. Pure optical imaging has much higher contrast ratio than ultrasound imaging, but permits only limited imaging up to a predetermined depth from a surface of a living tissue due to strong optical scattering inside soft tissues. On the other hand, ultrasound imaging provides a sufficiently high spatial resolution so as to examine a fetus. Photoacoustic imaging overcomes the drawback of optical imaging such as low imaging depths with conversion of optical energy into ultrasound waves due to a photoacoustic effect, thereby achieving both a high optical contrast ratio and a high spatial resolution.

Photoacoustic imaging techniques have already been developed significantly to conduct research on tumors, brains, hearts, and eyeballs of small animals. A photoacoustic imaging system may easily be integrated with a conventional ultrasound imaging system after undergoing only a slight modification such as removal of an ultrasound transmission function.

However, a photoacoustic diagnostic apparatus uses a laser for generating a short electromagnetic pulse whose absorption may cause a thermo-elastic expansion, and such a laser has significantly high optical energy.

SUMMARY

One or more embodiments of the present invention include a photoacoustic probe and a photoacoustic diagnostic apparatus including the photoacoustic probe, which are capable of blocking a laser emitted by the photoacoustic diagnostic apparatus due to inattention or mishandling of a user, or also due to machine defect when the photoacoustic diagnostic apparatus is not used for intended purposes.

Additional aspects will be set forth in part in the description which follows and, in part, will be apparent from the description, or may be learned by practice of the presented embodiments.

According to one or more embodiments of the present invention, a photoacoustic probe includes: an optical unit that includes an optical module and an optical window and irradiates an object with light through an optical window; an acoustic receiving unit that receives an acoustic wave generated from the object irradiated with the light; a shutter that is disposed between the optical module and the optical window and blocks light; a shutter driver that switches the shutter between a state in which the shutter is opened to allow light to pass therethrough (hereinafter, referred to as an "open state") and a state in which the shutter blocks the light (hereinafter, referred to as a "light-blocking state") according to whether an inspection starts.

The acoustic receiving unit may include an acoustic receiving window that is disposed in a front surface thereof to contact the object and through which the acoustic wave is incident, and the shutter driver may switch the shutter between the open state and the light-blocking state according to whether the acoustic receiving window is in contact with the object.

The photoacoustic probe may further include a button part including a button that moves between a projected position at which the button is located so as to protrude from the front surface and a retreated position at which the button is pushed from the object and retreated toward the front surface when the acoustic receiving window contacts the object; and an elastic member that applies an elastic force in a direction that the button part returns to the projected position. The shutter driver may be connected to the button part so as to switch the shutter to the open state and the light-blocking state as the button part moves to the retreated position and the projected position, respectively.

The shutter may include a shielding plate that is disposed to extend across an optical path between the optical module and the optical window. The shutter driver may include; a first rack gear connected to the button part;

a second rack gear connected to one end of the shielding plate; and at least one pinion gear for connecting the first rack gear with the second rack gear, wherein the shielding plate deviates from the optical path as the button part moves to the retreated position.

The at least one pinion gear may include at least one two-step gear for amplifying a movement displacement of the first rack gear.

The shielding plate may reflect light emitted by the optical module or scatter the light so that the light has an intensity less than or equal to a predetermined intensity.

The shutter may include a liquid crystal shutter, and the shutter driver may include a switch for sensing movement of the button part and a liquid crystal controller for controlling the liquid crystal shutter in response to a signal delivered from the switch.

According to one or more embodiments of the present invention, a photoacoustic diagnostic apparatus includes: a photoacoustic probe that irradiates an object with light and receives an acoustic wave generated from an inner tissue of the object by absorbing energy of the light; a main body including a control unit for controlling a diagnostic process based on the received acoustic wave; and a holder for mounting the photoacoustic probe, wherein the holder includes an opening through which the photoacoustic probe is inserted and a shielding portion that surrounds at least an optical window through which light emitted by the photoacoustic probe passes.

The shielding portion may reflect the light emitted by the photoacoustic probe or scatter the light so that the light has an intensity less than or equal to a predetermined intensity.

The photoacoustic diagnostic apparatus may further include a heat sink that is disposed on an outer wall of the shielding portion and dissipates away heat.

The holder may include a sensor for detecting whether the photoacoustic probe is placed in the holder.

The control unit may turn off the optical module when the sensor detects the photoacoustic probe.

The photoacoustic probe according to one or more embodiment of the present invention is configured to irradiate laser light through an optical unit only when an examiner diagnoses an object, thereby preventing laser light not intended by the examiner from being irradiated onto the object.

Furthermore, when the photoacoustic probe is placed in the holder, it is possible to block laser light emitted by the photoacoustic probe from passing through the holder to the object.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Exemplary embodiments will now be described more fully hereinafter with reference to the accompanying drawings so that they may be easily implemented by one of ordinary skill in the art. However, the present exemplary embodiments may have different forms and should not be construed as being limited to the descriptions set forth herein. Parts not related to the present invention are omitted for clarity of the description of the exemplary embodiments of the present invention. In the accompanying drawings, widths, lengths, thicknesses, etc. of components may be exaggerated for convenience, and like reference numerals refer to like elements throughout. Expressions such as "at least one of," when preceding a list of elements, modify the entire list of elements and do not modify the individual elements of the list.

Figure 1:
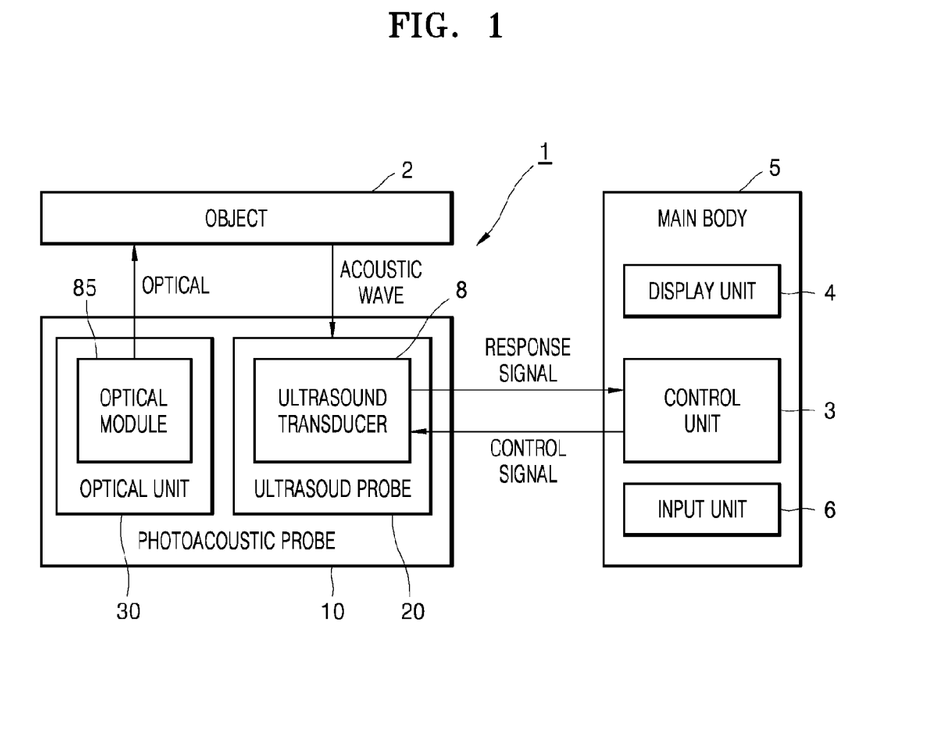
FIG. 1 is a block diagram of a main configuration of a photoacoustic diagnostic apparatus including a photoacoustic probe, according to an exemplary embodiment of the present invention.
Figure 2:
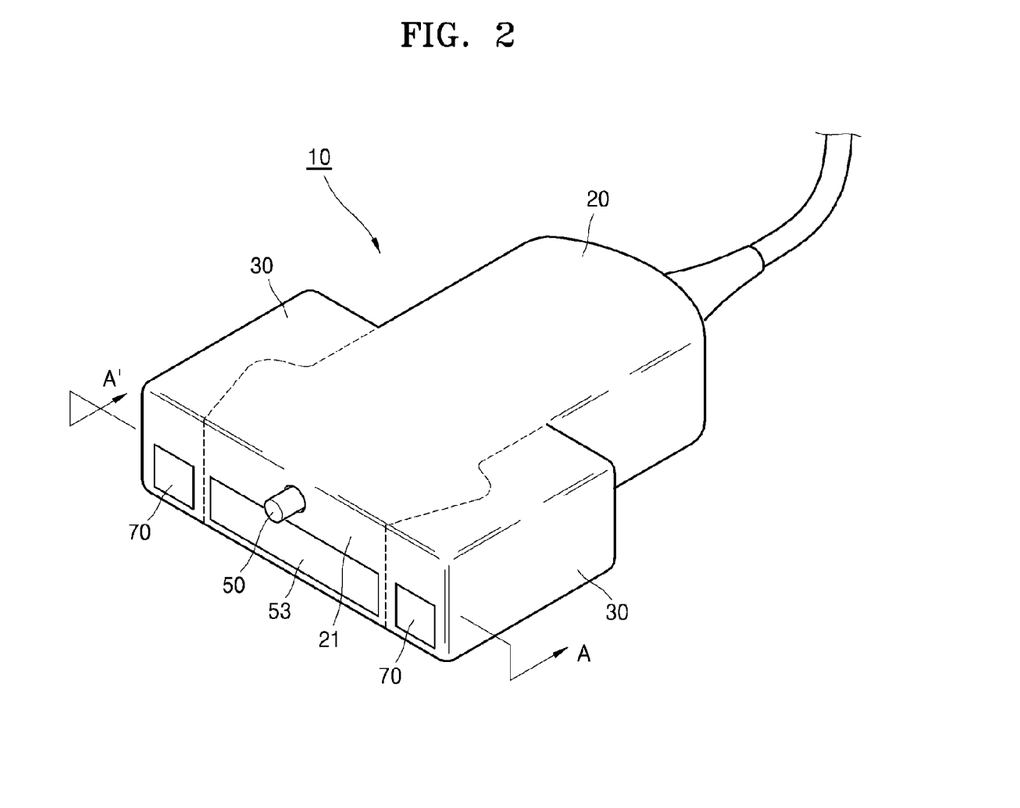
FIG. 2 is a perspective view of a photoacoustic probe according to an exemplary embodiment of the present invention.

FIG. 1 is a block diagram of a main configuration of a photoacoustic diagnostic apparatus 1 including a photoacoustic probe 10, according to an exemplary embodiment of the present invention, and FIG. 2 is a perspective view of a photoacoustic probe according to an exemplary embodiment of the present invention. Referring to FIGS. 1 and 2, the photoacoustic diagnostic apparatus 1 includes a main body 5 and the photoacoustic probe 10.

The main body 5 includes an input unit 6 for inputting manipulation commands necessary for operating the photoacoustic diagnostic apparatus 1, a control unit 3 for controlling the operation of the photoacoustic diagnostic apparatus 1, and a display unit 4 for visualizing an image signal received from the control unit 3.

The photoacoustic probe 10 is used to irradiate light toward an inner tissue of an object 2 and receive an acoustic wave generated from the tissue and includes an optical unit 30 and an acoustic wave receiver (hereinafter, referred to as an "ultrasound probe 20") equipped with an ultrasound transducer 8 for receiving acoustic waves. The photoacoustic probe 10 may irradiate light onto an inner part of the object 2 and receive acoustic waves therefrom while moving along a surface of the object 2 with its front surface being in contact with the surface of the object 2.

Manipulation commands related to diagnosis using the photoacoustic diagnostic apparatus 1, such as turning on or off the photoacoustic diagnostic apparatus 1, are input through the input unit 6. The input unit 6 may include buttons (not shown) and knobs (not shown) necessary for entering various manipulation commands.

The control unit 3 may detect characteristics of an inner tissue of the object 2 by using an ultrasound response signal received from the ultrasound probe 20 and form an image of the tissue by using the characteristics.

The display unit 4 visually displays the image of the tissue formed by the control unit 3. The display unit 4 may be realized by an image display device such as an electronic display board using a light-emitting diode (LED) technology, a liquid crystal display (LCD), or a cathode ray tube (CRT). The display unit 4 may be formed integrally with the main body 5 or separated therefrom.

The optical unit 30 is used to irradiate light toward the object 2. The optical unit 30 may include an optical module 85 having optical components related to emission of light, such as a light source, a mirror, a prism, a window, and a beam splitter. Light emitted by the optical module 85 may be irradiated onto the object 2 through an optical window 70. For example, the optical module 85 may be a laser output unit including an optical fiber (not shown). Light emitted by the optical module 85 causes a temperature increase and thus a thermal expansion within the object 2, which generates acoustic waves from the object 2.

A conventional ultrasound probe transmits an ultrasound wave into an object and receives a response signal reflected back from each inner tissue of the object via an ultrasound transducer. On the other hand, the ultrasound probe 20 for use in the photoacoustic probe 10 according to the present embodiment receives an acoustic signal that is generated from each inner tissue of the object 2 due to light emitted from the optical unit 30 and returned from the tissue through the ultrasound transducer 8. The ultrasound transducer 8 converts the acoustic signal into an electrical signal by using a piezoelectric or magnetostrictive effect and transmits the electrical signal to the control unit 3. For example, the ultrasound transducer 8 may be a piezoelectric micromachined ultrasonic transducer (pMUT), a capacitive micromachined ultrasonic transducer (cMUT), or magnetic micromachined ultrasonic transducer (mMUT).

Figure 3:
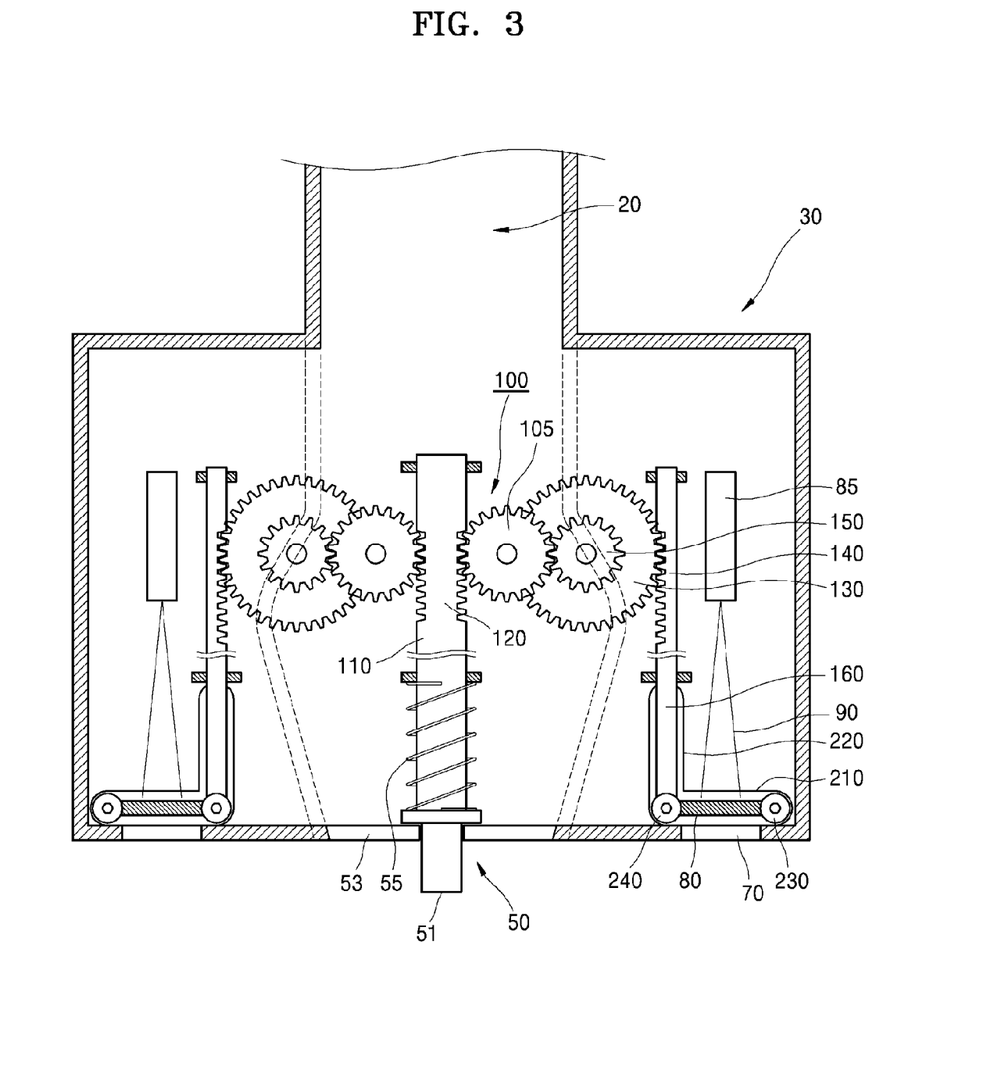
FIG. 3 is a cross-sectional view taken along line A-A' of FIG. 2.

FIG. 3 is a cross-sectional view of the photoacoustic probe 10 taken along line A-A' of FIG. 2. Referring to FIGS. 2 and 3, the photoacoustic probe 10 may include the ultrasound probe 20 and the optical unit 30. The optical unit 30 may be disposed at one or both sides of the ultrasound probe 20.

As described above, an acoustic receiving window 53 may be disposed in a front surface 21 of the ultrasound probe 20. An acoustic wave generated from each inner tissue of the object 2 enters the ultrasound transducer 8 through the acoustic receiving window 53.

For photoacoustic inspection, the front surface 21, specifically, the acoustic receiving window 53 of the photoacoustic probe 10 is in contact with the object 2. Since the photoacoustic probe 10 uses light having a short electromagnetic pulse such as laser light having a high energy strength, a safety device is needed to prevent unintended emission of light through the optical window 70. To achieve this, the optical unit 30 includes a shutter 80 that is disposed between the optical module 85 and the optical window 70 and made of a material that can block light by reflecting the same or reduce the intensity of the light to that less than or equal to a predetermined intensity by scattering the light. The shutter 80 may be a liquid crystal shutter that can selectively switch between a state in which a liquid crystal blocks light ("light-blocking state") and a state in which a liquid crystal allows light to pass therethrough (light-transmission state") in response to an electrical signal. A shutter driver 100 switches the shutter 80 between a light-transmission state and a light-blocking state according to whether the inspection starts.

In one embodiment, according to a configuration in which the start of the inspection is determined according to whether the acoustic receiving window 53 is in contact with the object 2, it is possible to prevent light from escaping through the optical window 70 when the photoacoustic probe 10 does not contact the object 2.

In detail, referring to FIGS. 2 and 3, whether the acoustic receiving window 53 is in contact with the object 2 may be detected by a button part 50 that is pressed in or stuck out of the front surface 21. The button part 50 that has a button 51 projecting out from the front surface 21 connects to the shutter driver 100. An elastic member 55 applies an elastic force to the button part 50 in a direction that the button 51 is projected from the front surface 21.

When an inspection is not performed, i.e., when the acoustic receiving window 53 is separated from the object 2, the button 51 is located at a projected position so as to protrude from the front surface 21 more than the acoustic receiving window 53. When the photoacoustic probe 10 moves close to the object 2 for inspection, the button 51 contacts the object 2 before the acoustic receiving window 53 touches the object 2 and then is pushed in an opposite direction of the elastic force. When the acoustic receiving window 53 subsequently contacts the object 2, the button part 50 is located at a retreated position that it is completely retreated toward the front surface 21. When the photoacoustic probe 10 is separated from the object 2 after completing the inspection, the button part 50 returns to a projected position due to an elastic force exerted by the elastic member 55.

The button part 50 may be disposed so as not to interfere with acoustic receiving window 53 and the optical window 70. In the present embodiment, the button part 50 is located near the acoustic receiving window 53. Due to this configuration, it is possible to accurately determine whether the acoustic receiving window 53 is in contact with the object 2.

The shutter driver 100 drives the shutter 80 by using movement of the button part 50. The shutter driver 100 may drive the shutter 80 either mechanically or by using an electrical signal.

In one embodiment, the shutter driver 100 may drive the shutter 80 by using a plurality of gears and a plurality of connecting rods. The shutter driver 100 includes first and second connecting rods 110 and 160, first and second rack gears 120 and 140, and one or more pinion gears. The one or more pinion gears may include one or more two-step gears for amplifying movement displacement of the first rack gear 120.

In one embodiment, the one or more pinion gears may include first through third pinion gears 105, 130, and 150. The second and third pinion gears 130 and 150 are two-step gears for amplifying movement displacement of the first rack gear 120. This construction causes the second rack gear 140 to move in the same direction as the first rack gear 120.

The first connecting rod 110 is connected to the button part 50 so as to move in the same directions that the button part 50 moves into and out of the front surface 21. The first rack gear 120 is provided along the first connecting rod 110. The second connecting rod 160 is disposed parallel to the first connecting rod 110 and includes the second rack gear 140. The first and second rack gears 120 and 140 are connected to each other by the first through third pinion gears 105, 130, and 150. The first rack gear 120 meshes with the first pinion gear 105, and a direction that the first pinion gear 105 rotates may be determined according to the direction of a linear motion of the first rack gear 120. The third pinion gear 150 meshes with the first pinion gear 105, and rotates in the opposite direction to the direction of rotation of the first pinion gear 105. The second and third pinion gears 130 and 150 are formed integrally with each other so that they rotate around the same rotation axis 135. Thus, the second and third pinion gears 130 and 150 rotate in the same direction. Since the third pinion gear 150 has a smaller diameter than the second pinion gear 130 or the number of the teeth of the third pinion gear 150 and the second pinion gear 130 is adjusted, it is possible to replace movement of the button part 50 having a small size with movement of the shutter 80 having a large size. The second pinion gear 130 meshes with the second rack gear 140, and the direction of a linear motion of the second rack gear 140 is determined according to the direction that the second pinion gear 130 rotates.

Figure 4:
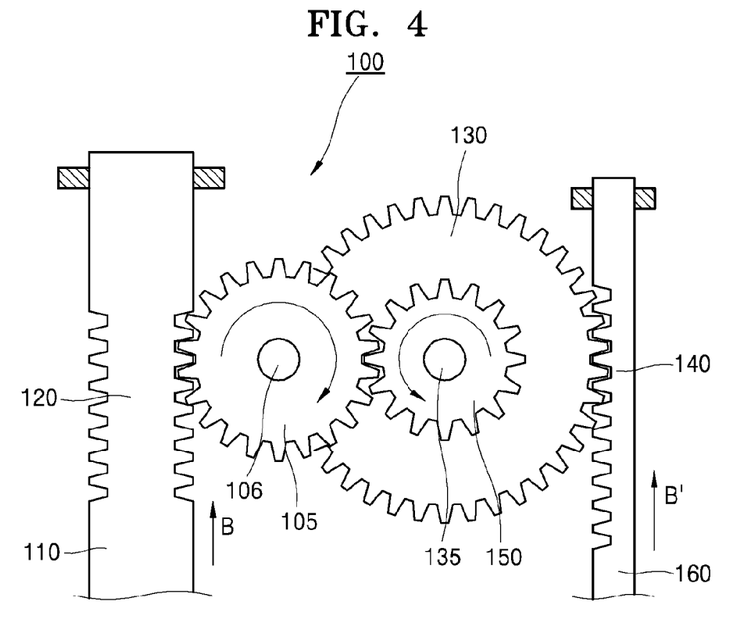
FIG. 4 is detailed diagram of a shutter driver shown in FIG. 3.

FIG. 4 is a cross-sectional view of the shutter driver 100 shown in FIG. 3. Referring to FIG. 4, as the acoustic receiving window 53 contacts the object 2, the button part 50 linearly moves in a direction indicated by an arrow B. The linear motion of the button part 50 is then transmitted to the first rack gear 120 by the first connecting rod 110, so that the first pinion gear 105 meshing with the first rack gear 120 rotates clockwise. The first pinion gear 105 causes the second and third pinion gears 130 and 150 to rotate counterclockwise. The second rack gear 140 converts a rotational motion of the third pinion gear 130 into a linear motion, so that the second connecting rod 160 linearly moves in a direction indicated by an arrow B'. Although not shown in FIG. 4, when the acoustic receiving window 53 is separated from the object 2, the button part 50 linearly moves in a direction opposite to the direction indicated by arrow B due to an elastic force exerted by the elastic member 55. The linear motion of the button part 50 is then transmitted to the first connecting rod 110, the first rack gear 120, the first through third pinion gears 105, 130, and 150, the second rack gear 140, and the second connecting rod 160, and the second connecting rod 160 moves in a direction opposite to the direction indicated by arrow B'.

Figure 5A:
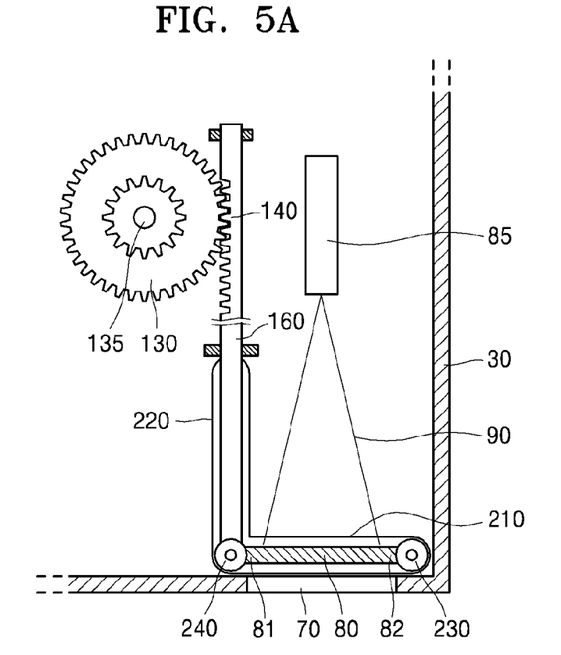
FIG. 5A illustrates a state in which light emitted by an optical module is blocked by a shutter in an optical unit shown in FIG. 3.
Figure 5B:
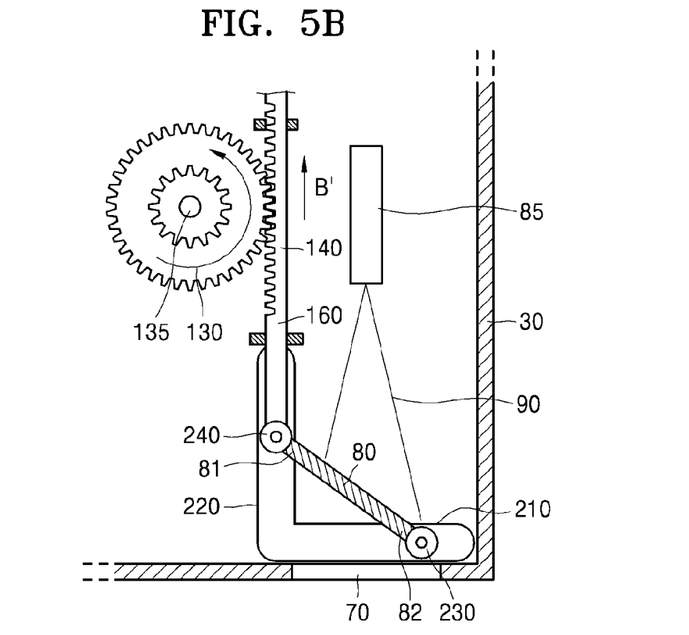
FIG. 5B illustrates a state in which the shutter is moved by the shutter driver in the optical unit shown in FIG. 3.
Figure 5C:
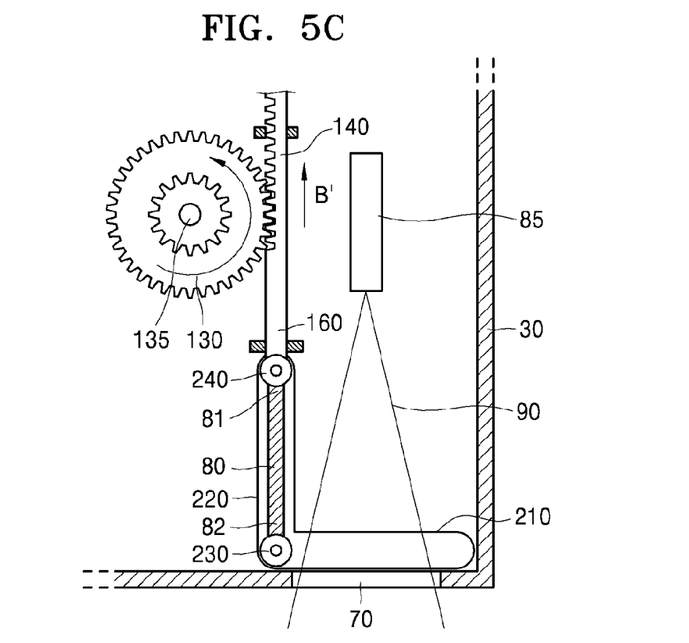
FIG. 5C illustrates a state in which the shutter is opened by the shutter driver in the optical unit shown in FIG. 3.

FIGS. 5A through 5C are cross-sectional views of the optical unit 30 of FIG. 3, illustrating a process whereby the optical window 70 shielded by the shutter 80 opens as an inspection starts. Referring to FIGS. 5A through 5C, the shutter 80 is formed by a shielding plate that is disposed to extend across an optical path between the optical module 85 and the optical window 70. The second connecting rod 160 is connected to one end 81 of the shutter 80 to form a link structure.

When the acoustic receiving window 53 is separated from the object 2, as shown in FIG. 5A, the shutter 80 is disposed between the optical window 70 and the optical module 85, and thus blocks light that is emitted from the optical module 85. As the acoustic receiving window 53 moves closer to the object 2, the button part 50 moves in the direction indicated by arrow B, and the second connecting rod 160 moves in the direction indicated by arrow B'. Then, as shown in FIG. 5B, the one end 81 of the shutter 80 is pulled up in the direction indicated by arrow B' that the second connecting rod 160 moves. The other end 82 of the shutter 80 moves in a direction that intersects the direction that the one end 81 thereof moves so that the optical window 70 begins to gradually open. When the acoustic receiving window 53 contacts the object 2, as shown in FIG. 5C, the shutter 80 completely deviates from the optical path between the optical module 85 and the optical window 70 so that it is at a position that allows light to pass through the optical window 70. Thus, light 90 exiting the optical module 85 may pass through the optical window 70 before being irradiated onto the object 2.

In one embodiment, the optical unit 30 includes a first guide 210 for defining a movement path of the other end 82 of the shutter 80. The first guide 210 extends in a direction intersecting (e.g., perpendicular to) the direction that the one end 81 of the shutter 80 moves and has a slot shape into which the other end 82 of the shutter 80 is inserted. A rotatable first roller 230 is provided at the other end 82 of the shutter 80 so that the other end 82 may move smoothly along the first guide 210.

In one embodiment, a second guide 220 may also be provided to define a movement path of the one end 81 of the shutter 80 and has a slot shape into which the one end 81 of the shutter 80 is inserted. A rotatable second roller 240 is disposed at the one end 81 of the shutter 80 so that the one end 81 may move smoothly along the second guide 220.

Figure 6:
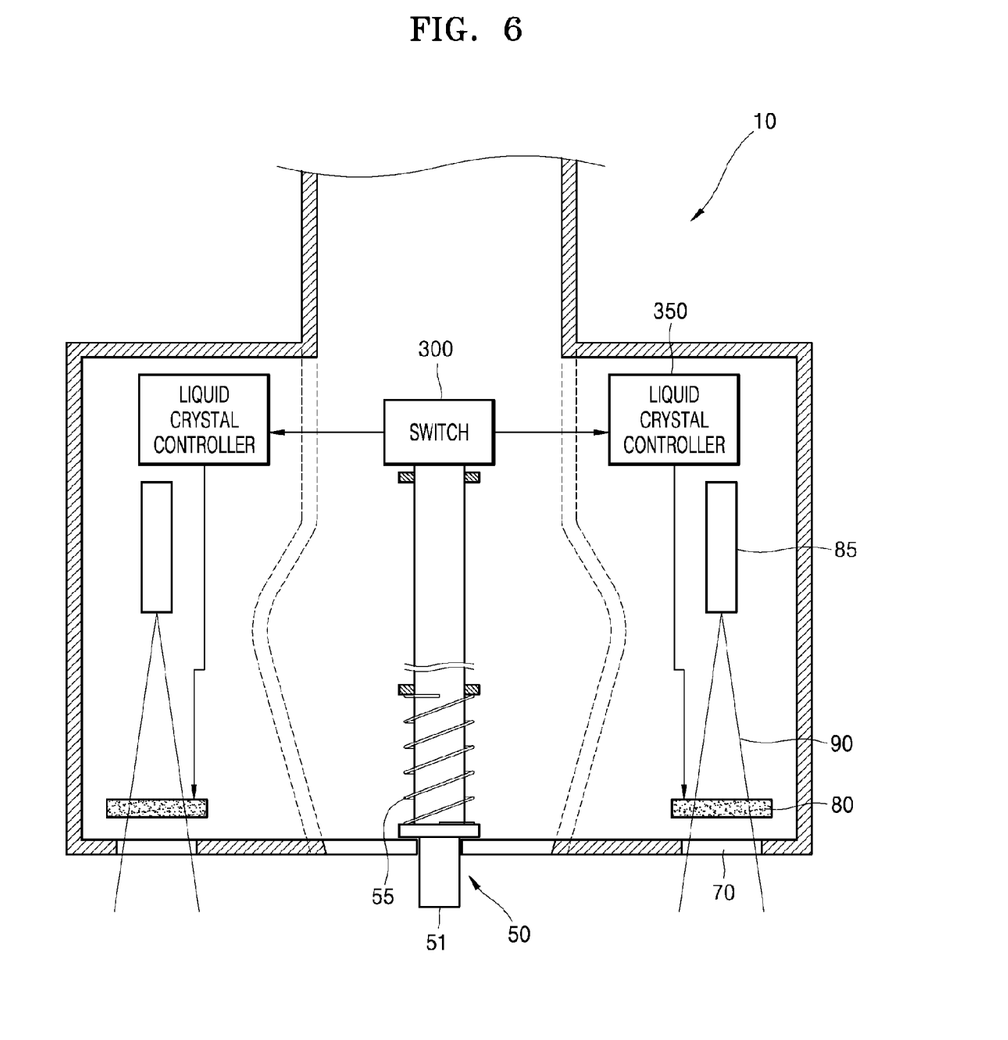
FIG. 6 is a cross-sectional view of a photoacoustic probe according to another exemplary embodiment of the present invention.

FIG. 6 is a cross-sectional view of a photoacoustic probe 10 according to another exemplary embodiment of the present invention. Referring to FIG. 6, the photoacoustic probe 10 according to the present embodiment includes a liquid crystal shutter as the shutter 80. The shutter driver (100 in FIG. 3) includes a button part 50, a switch 300 that is turned on or off by the button part 50, and a liquid crystal controller 350 for driving the shutter 80 in response to on/off signals of the switch 300.

The switch 300 is disposed within the photoacoustic probe 10 and connected to the button part 50. The switch 300 is turned on or off according to movement of the button part 50 that varies depending on whether the acoustic receiving window 53 is in contact with the object 2. The liquid crystal controller 350 is electrically connected to the switch 300 and determines the orientation of liquid crystals in the shutter 80 according to an electrical signal delivered from the switch 300. For example, the orientation of the liquid crystals may change in response to an applied voltage so as to allow light 90 to pass therethrough or block light. By using properties of the liquid crystals, it is possible to electrically control transmission/non-transmission of the light 90.

Figure 7A:
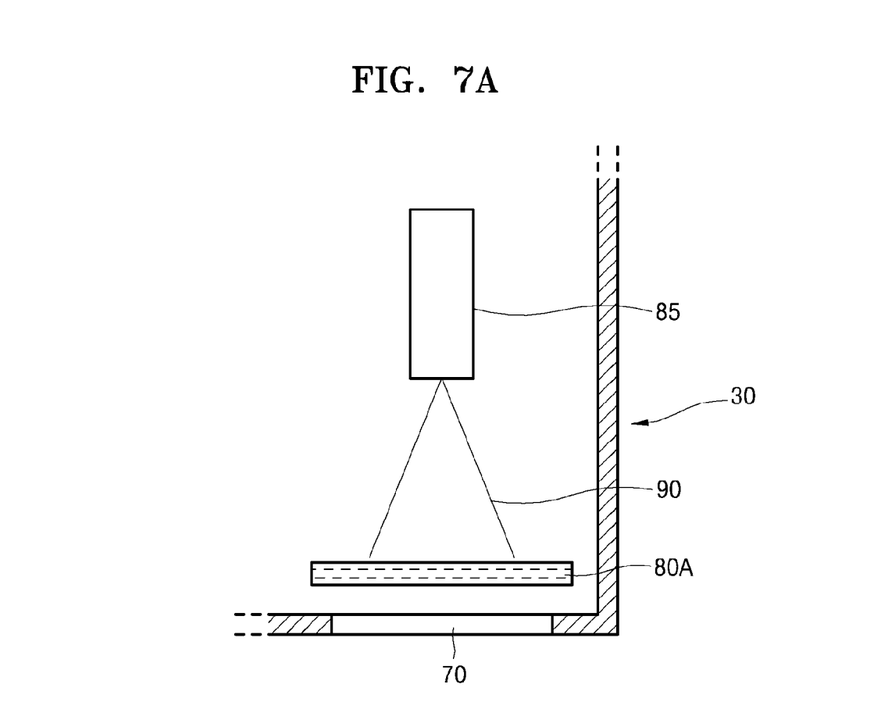
FIG. 7A illustrates a state in which light emitted by an optical module is blocked by a liquid crystal shutter in an optical unit shown in FIG. 6.
Figure 7B:
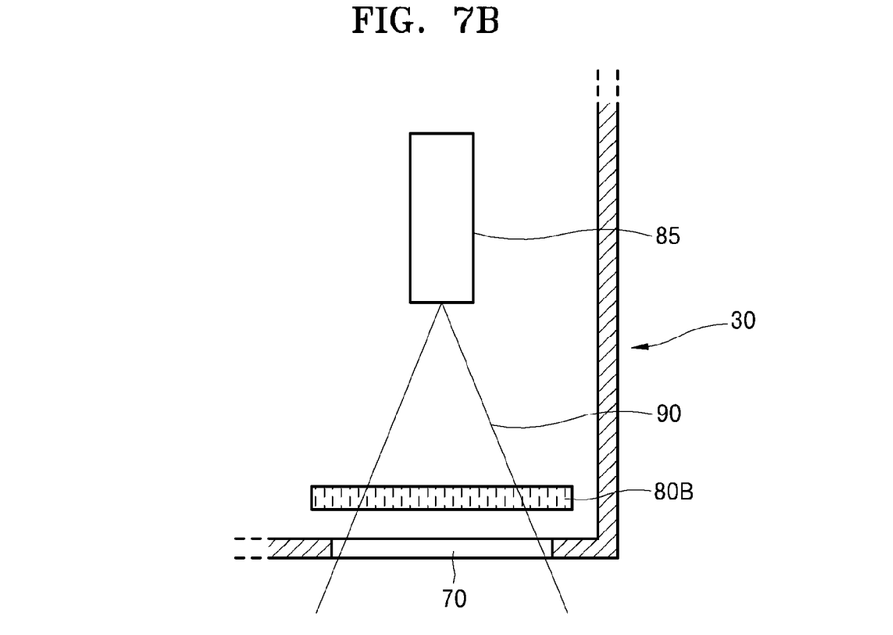
FIG. 7B illustrates a state in which light emitted from an optical module passes through a liquid crystal shutter in the optical unit shown in FIG. 6.

FIGS. 7A and 7B are cross-sectional views illustrating states in which light 90 emitted by the optical module 85 is blocked and transmitted by the shutter 80 in the optical unit 30 shown in FIG. 6, respectively, according to an exemplary embodiment of the present invention.

Referring to FIG. 7A, if the acoustic receiving window 53 does not contact the object 2, the button 51 of the button part 50 remains protruding from the front surface 21, and the switch 300 maintains a first state (off-state). When the switch 300 is in the first state, the liquid crystal controller 350 does not apply an electrical signal to liquid crystals 80A in the shutter 80. Thus, the liquid crystals 80A in the shutter 80 are interwined to prevent light from passing therethrough, which blocks an optical path between the optical module 85 and the optical window 70.

Referring to FIG. 7B, when the acoustic receiving window 53 is brought into contact with the object 2 with the start of inspection of an object, the button part 50 is moved, and the switch 300 changes to a second state (on-state). When the switch 300 is in the second state, the liquid crystal controller 350 applies an electrical signal to liquid crystals 80B in the shutter 80 so that the liquid crystals 80B forms a crystal structure in a uniform direction, thereby allowing light to pass therethrough. Thus, an optical path between the optical module 85 and the optical window 70 is opened.

Figure 8:
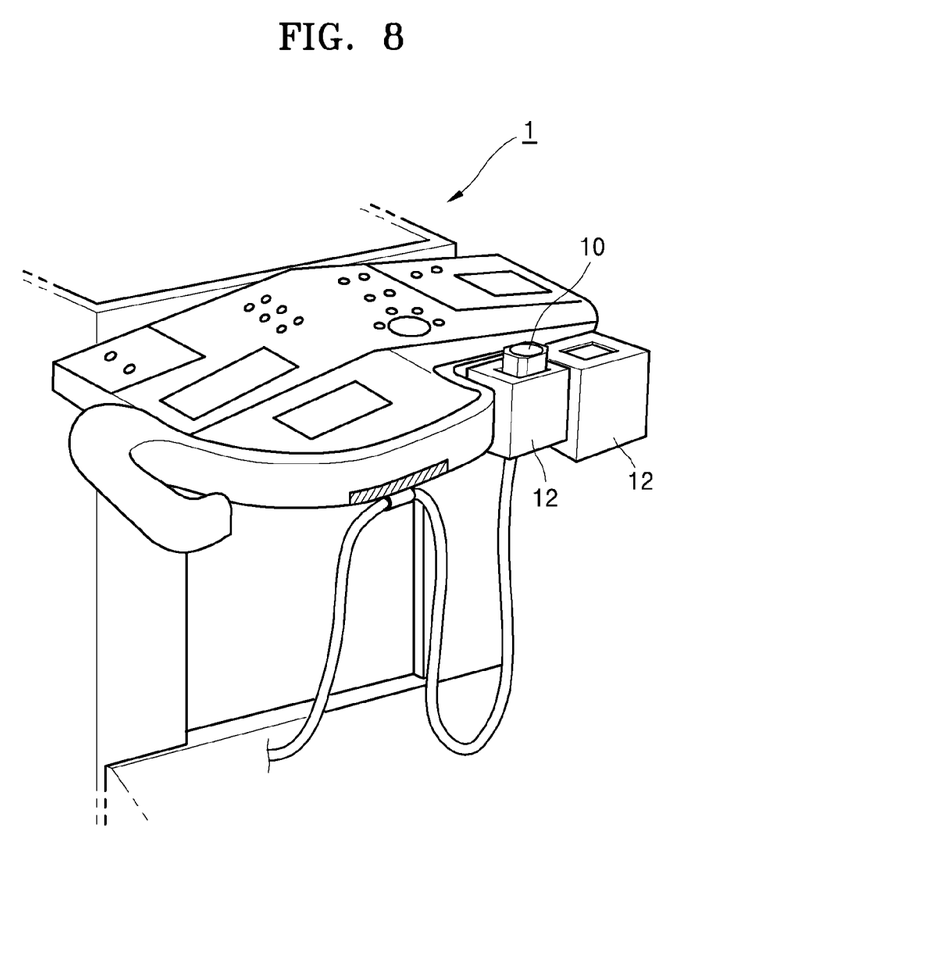
FIG. 8 is a partial perspective view of a photoacoustic diagnostic apparatus equipped with a photoacoustic probe holder, according to an exemplary embodiment of the present invention.

FIG. 8 is a partial perspective view of the photoacoustic diagnostic apparatus 1 of FIG. 1 equipped with a photoacoustic probe holder 12 according to an exemplary embodiment of the present invention. Referring to FIGS. 1 and 8, the photoacoustic diagnostic apparatus 1 according to the present embodiment includes the photoacoustic probe 10 and the photoacoustic probe holder 12 mounted on the main body 5. An examiner uses the photoacoustic probe 10 to diagnose the object 2. If the photoacoustic probe 10 is not used, the photoacoustic probe 10 may be seated on the photoacoustic probe holder 12.

Figure 9:
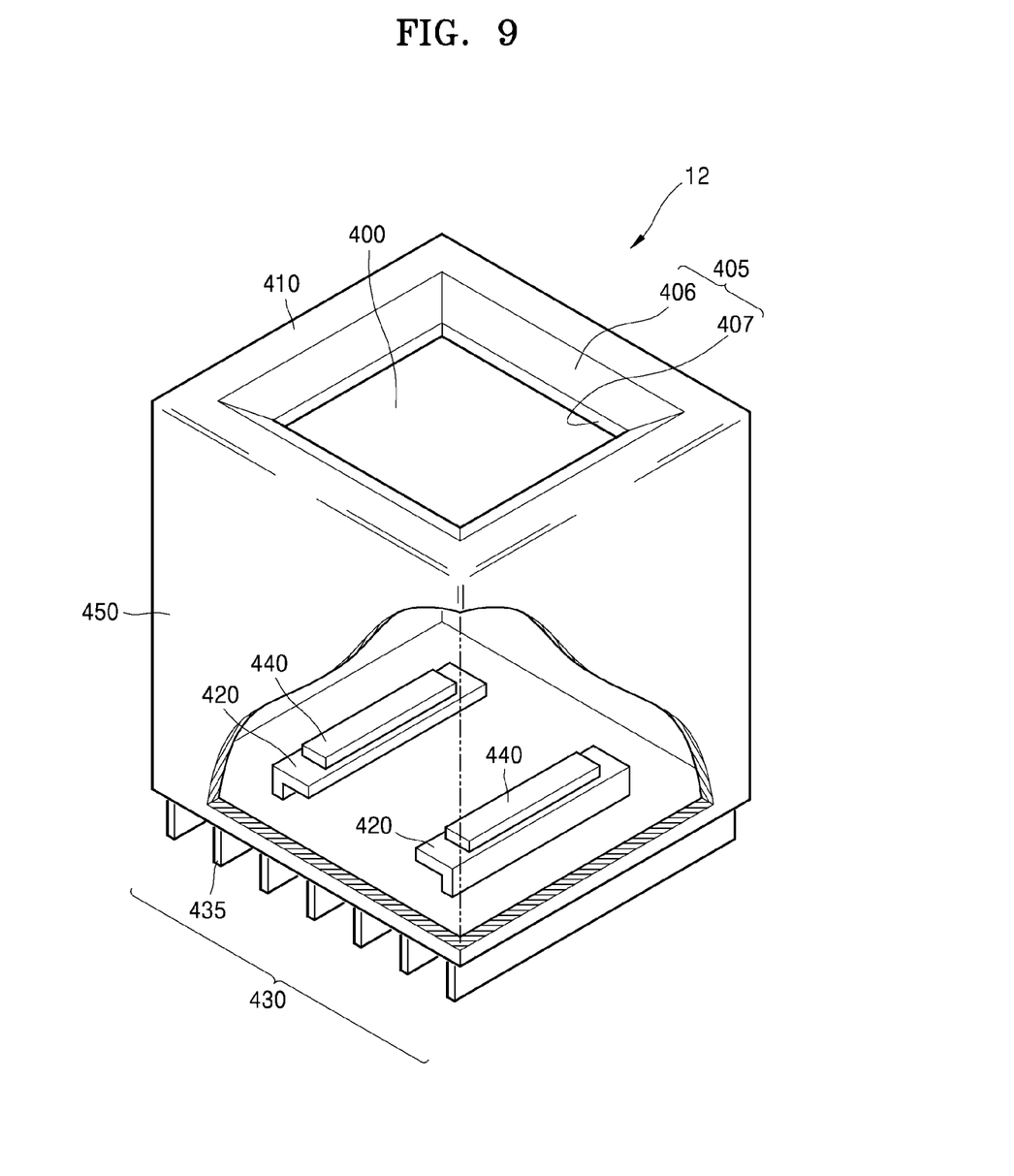
FIG. 9 is a perspective view of a photoacoustic probe holder according to an exemplary embodiment of the present invention.
Figure 10:
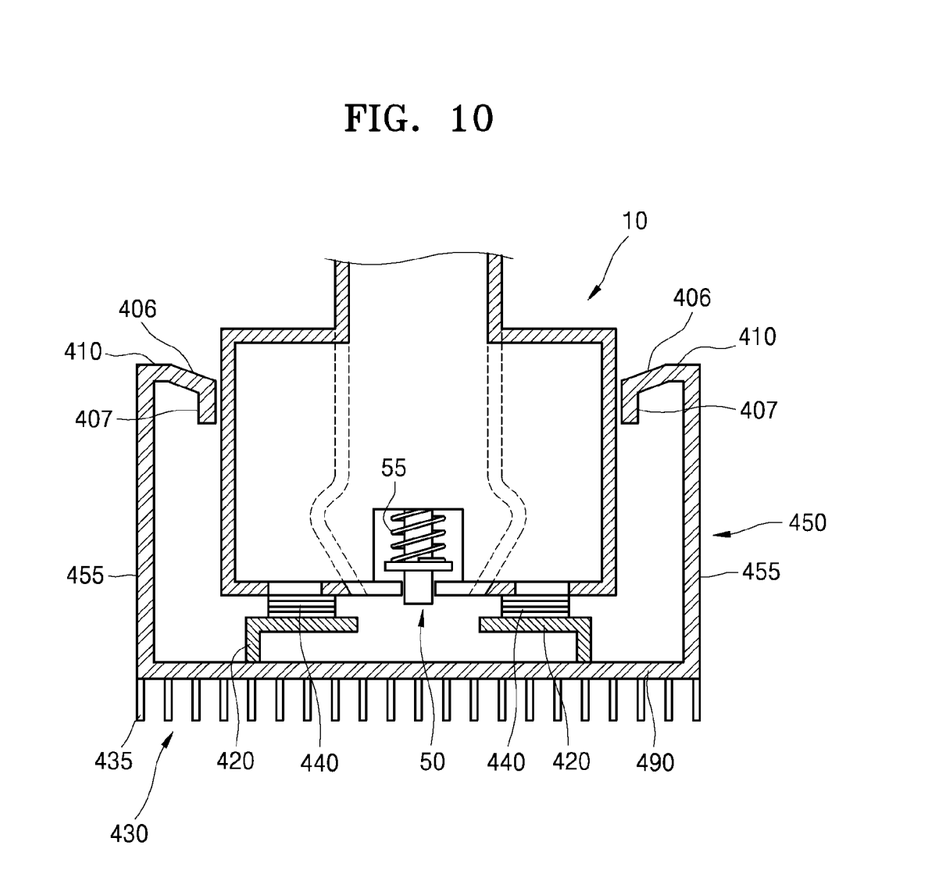
FIG. 10 is a cross-sectional view illustrating a state in which a photoacoustic probe is mounted in the photoacoustic probe holder shown in FIG. 8, according to an exemplary embodiment of the present invention.

FIG. 9 is a perspective view of a photoacoustic probe holder 12 according to an exemplary embodiment of the present invention, and FIG. 10 is a cross-sectional view of the photoacoustic probe holder 12 in which the photoacoustic probe 10 is mounted, according to an exemplary embodiment of the present invention.

Referring to FIGS. 9 and 10, the photoacoustic probe holder 12 includes an opening 400 through which the photoacoustic probe 10 is inserted, a guide 405 for guiding the photoacoustic probe 10 so that the photoacoustic probe 10 is inserted through the opening 400, a shielding portion 450 that encloses the photoacoustic probe 10 up to a predetermined height from a bottom part of the photoacoustic probe 10, i.e., the acoustic receiving window 53 and the optical window 70.

The opening 400 is formed in a ceiling portion 410 of the photoacoustic probe 12. The size of the opening 400 is determined to match to a size of the bottom part of the photoacoustic probe 10.

The guide 405 forms an edge of the opening 400 and includes an inclined portion 406 that is formed obliquely to the ceiling portion 410 so as to facilitate insertion of the photoacoustic probe 10 into the opening 400 and an extension portion 407 that extends down from the inclined portion 406.

The shielding portion 450 has an entirely rectangular parallelepiped shape including four side surfaces 455, a bottom surface 490, and the ceiling portion 410, but is not limited thereto. The shielding portion 450 may have any other shape such as a cylindrical shape that can entirely cover the photoacoustic probe 10. When the photoacoustic probe 10 is placed in the photoacoustic probe holder 12, the shielding portion 450 may be disposed so as to surround the bottom part of the photoacoustic probe 10. The shielding portion 450 may be formed of a material that can reflect light emitted by the photoacoustic probe or scatter the light so that the light has an intensity less than or equal to a predetermined intensity. A pair of supports 420 may be provided on the bottom surface 490 so as not to interfere with the button part 50 when the photoacoustic probe is placed in the photoacoustic probe holder 12. In other words, the pair of supports 420 includes a shelter for hiding the button part 50. In one embodiment, as shown in FIG. 9, the pair of supports 420 are separated from each other so that a space therebetween functions as the shelter, but are not limited thereto. The pair of supports 420 may be formed integrally with each other and have a hollow hole for hiding the button part 50 at a central portion thereof.

The photoacoustic probe holder 12 may further include a heat sink 430 that may be disposed on at least one outer wall of the shielding portion 450. When light is emitted from the photoacoustic probe 10 placed in the photoacoustic probe holder 12, light is reflected or scattered by the shielding portion 450, thereby causing heat to be generated within or on the photoacoustic probe holder 12. The generated heat is dissipated into the air by the heat sink 430 disposed on the photoacoustic probe holder 12. In one embodiment, the heat sink 430 includes a plurality of heat sinking fins 435 and is disposed on an outer circumference of the bottom surface 490.

The photoacoustic probe holder 12 may further include at least one sensor 440 for detecting whether the photoacoustic probe 10 is seated in the photoacoustic probe holder 12. The at least one sensor 440 may be disposed along at least one inner wall of the shielding portion 450, but is not limited thereto. The photoacoustic probe 10 needs to move close to the photoacoustic probe holder 12 so that it is seated in the photoacoustic probe holder 12. Since mounting of the photoacoustic probe 10 in the photoacoustic probe holder 12 may be determined according to whether the photoacoustic probe 10 moves close thereto, the sensor 440 may be used to detect whether the photoacoustic probe 10 is seated in the photoacoustic probe holder 12. For example, the sensor 440 may be a weight sensor for sensing a weight of the photoacoustic probe 10, a piezoelectric sensor pressed by the photoacoustic probe 10, a micro switch, an optical sensor, or the like.

Figure 11:
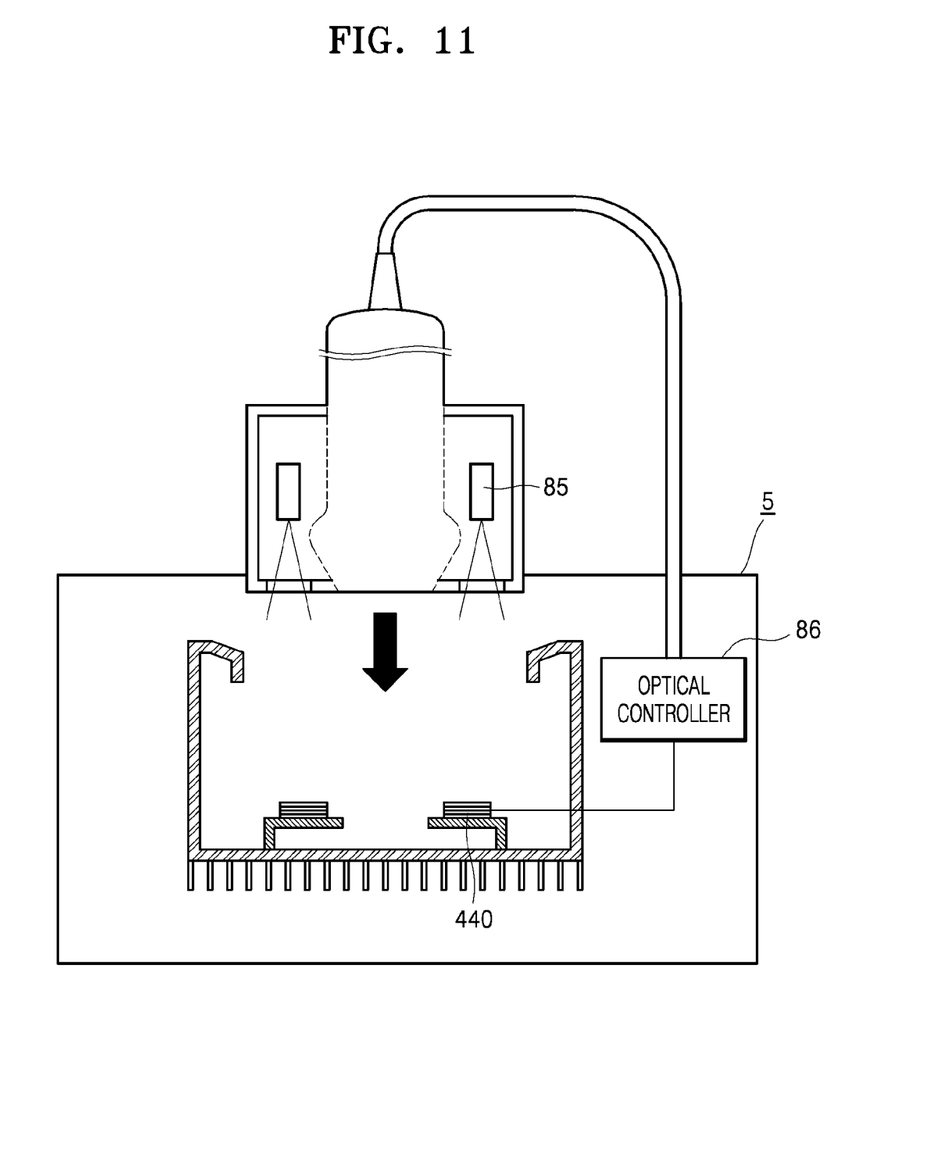
FIG. 11 is a cross-sectional view illustrating a process of mounting a photoacoustic probe in the photoacoustic probe holder shown in FIG. 8, according to an exemplary embodiment of the present invention.

When the photoacoustic probe 10 is seated in the photoacoustic probe holder 12, the optical module 85 is switched off so as to prevent emission of light form the optical module 85. Referring to FIG. 11, the main body 5 may further include an optical controller 86. For example, the sensor 440 disposed in the photoacoustic probe holder 12 may be connected to the optical controller 86 in the main body 5. When the sensor 440 detects that the photoacoustic probe 10 is seated in the photoacoustic probe holder 12, the optical controller 86 may switch off the optical module 85 so as to prevent light from being emitted from the optical module 85.

While one or more embodiments of the present invention have been described with reference to the figures, it should be understood that the embodiments described therein should be considered in a descriptive sense only and not for purposes of limitation. Descriptions of features or aspects within each embodiment should typically be considered as available for other similar features or aspects in other embodiments. It will also be understood by those of ordinary skill in the art that various changes in form and details may be made therein without departing from the spirit and scope of the present invention as defined by the following claims.

What is claimed is:

1. A photoacoustic probe comprising:
an optical unit comprising an optical module and an optical window, the optical module irradiates an object with light through the optical window;
an acoustic receiving unit that receives an acoustic wave generated from the object irradiated with the light;
a shutter that is disposed between the optical module and the optical window and blocks light;
a shutter driver that switches the shutter between an open state in which the shutter is opened to allow light to pass therethrough and a light-blocking state in which the shutter blocks the light;
a first guide defining a movement path of one end of the shutter, the first guide extending in a first direction and having a slot shape into which the one end of the shutter is inserted;
a second guide defining a movement path of another end of the shutter, the second guide extending in a direction perpendicular to the first direction and having a slot shape in to which the another end of the shutter is inserted;
a rotatable first roller disposed at the one end of the shutter and inserted into the first guide; and
a rotatable second roller disposed at the another end of the shutter and inserted into the second guide,
wherein the acoustic receiving unit comprises an acoustic receiving window that is disposed in a front surface thereof to contact the object and through which the acoustic wave is incident, the acoustic receiving window being spaced apart from the optical window, and
wherein the shutter driver switches the shutter from the light-block state to the open state according to whether the acoustic receiving window is in contact with the object.

2. The photoacoustic probe of claim 1, further comprising:
- a button part configured to move between a projected position at which the button part is located so as to protrude from the front surface and a retreated position at which the button part is pushed from the object and retreated toward the front surface when the acoustic receiving window contacts the object; and
- an elastic member that applies an elastic force to the button part in a direction that causes the button part to return to the projected position,
- wherein the shutter driver is connected to the button part so as to switch the shutter to the open state and the light-blocking state as the button part moves to the retreated position and the projected position, respectively.

3. The photoacoustic probe of claim 2, wherein the shutter comprises a shielding plate that is disposed to extend across an optical path between the optical module and the optical window,
- wherein the shutter driver comprises:
    - a first rack gear connected to the button part;
    - a second rack gear connected to one end of the shielding plate; and
    - at least one pinion gear for connecting the first rack gear with the second rack gear, wherein the shielding plate deviates from the optical path as the button part moves to the retreated position.

4. The photoacoustic probe of claim 3, wherein the at least one pinion gear comprises at least one two-step gear for amplifying a movement displacement of the first rack gear.

* * * * *